(12) United States Patent
Langley et al.

(10) Patent No.: US 9,732,019 B1
(45) Date of Patent: Aug. 15, 2017

(54) SYSTEM AND METHOD TO REMOVE ORGANIC ACID FROM A RICH MEG STREAM BY STRIPPING

(71) Applicant: Cameron Solutions, Inc., Houston, TX (US)

(72) Inventors: Steven Langley, Croydon (GB); David John Knight, Kuala Lumpur (MY)

(73) Assignee: Cameron Solutions, Inc., Houston, TX (US)

( * ) Notice: Subject to any disclaimer, the term of this patent is extended or adjusted under 35 U.S.C. 154(b) by 0 days.

(21) Appl. No.: 15/089,076

(22) Filed: Apr. 1, 2016

(51) Int. Cl.
| | |
|---|---|
| *C07C 29/76* | (2006.01) |
| *B01D 3/00* | (2006.01) |
| *B01D 53/00* | (2006.01) |
| *B01D 3/34* | (2006.01) |
| *B01D 53/72* | (2006.01) |
| *B01D 53/78* | (2006.01) |

(52) U.S. Cl.
CPC .............. *C07C 29/76* (2013.01); *B01D 3/343* (2013.01); *B01D 53/72* (2013.01); *B01D 53/78* (2013.01)

(58) Field of Classification Search
CPC .......... C07C 29/76; B01D 3/343; B01D 53/78
USPC ....................................................... 568/868
See application file for complete search history.

(56) References Cited

U.S. PATENT DOCUMENTS

| 4,898,644 A | 2/1990 | Van Horn |
| 2015/0104356 A1 | 4/2015 | Messenger |
| 2015/0119609 A1 | 4/2015 | Deshmukh |

FOREIGN PATENT DOCUMENTS

| EP | 2860168 | 4/2015 |

*Primary Examiner* — Sikarl Witherspoon
(74) *Attorney, Agent, or Firm* — Gable Gotwals

(57) ABSTRACT

A system and method for removing acetic acid and other short chain fatty acids described as organic acid from a rich mono-ethylene glycol ("MEG") solution does so by stripping the organic acid from the rich MEG solution by contacting the solution with a gas, the gas being nitrogen or a fuel gas such as methane; and stripping the organic acid from the gas by contacting the gas with a caustic solution such as a dilute sodium hydroxide solution. The stripping takes place in respective stripping columns. A portion of the gas exiting the gas/organic acid stripping column can be recycled to the MEG/organic acid stripping column to reduce total gas usage. A portion of the waste stream exiting the gas/organic acid stripping column can be recycled back to the gas/organic acid stripping column to reduce the amount of caustic solution used as well as the amount of waste.

12 Claims, 2 Drawing Sheets

*FIG. 2*

| Names | Units | Rich MEG with Acetic | Rich MEG | Gas make-up | Gas/acetic | Gas purge | Gas recycle | Caustic Solution | Waste Water / Acetic |
|---|---|---|---|---|---|---|---|---|---|
| Temperature | °C | 60.0 | 59.0 | 40.0 | 60.0 | 41.5 | 41.5 | 40.2 | 41.9 |
| Pressure | bar | 2.0 | 2.1 | 3.9 | 2.0 | 2.1 | 2.1 | 5.5 | 5.5 |
| Mass Flow | kg/h | 52213 | 52068 | 100 | 1245.6 | 108.0 | 1000 | 5000 | 5137.6 |
| Volumetric Flow | m³/h | 50.85 | 50.68 | 40.79 | 967.31 | 79.12 | 732.49 | 5.00 | 5.13 |
| Mass Density | kg/m³ | 1026.8 | 1027.4 | 2.45 | 1.29 | 1.37 | 1.37 | 1000.7 | 1001.9 |
| Water(Mass Fraction) | % | 59.90 | 59.90 | - | 8.53 | 4.04 | 4.04 | 99.00 | 97.5 |
| MEG(Mass Fraction) | % | 39.90 | 40.00 | - | 0.06 | 23.6 ppbW | 23.6 ppbW | - | 135 ppmW |
| NaOH(Mass Fraction) | % | 0.00 | 0.00 | - | 0.00 | 0.00 | 0.00 | 1.00 | 0.973 |
| Acetic Acid(Mass Fraction) | ppm | 1497 | 94.77 | - | 58310 | 0.01823 | 0.01823 | - | 14260 |
| Propionic Acid(Mass Fraction) | ppm | 89.85 | 38.22 | - | 19990 | 22190 | 22190 | - | 59.1 |
| Formic Acid(Mass Fraction) | ppm | 29.95 | 0.06561 | - | 1253 | 0.0001793 | 0.0001793 | - | 303.7 |
| Butyric Acid(Mass Fraction) | ppm | 69.89 | 19.63 | - | 20480 | 22890 | 22890 | - | 30.2 |

SYSTEM AND METHOD TO REMOVE ORGANIC ACID FROM A RICH MEG STREAM BY STRIPPING

BACKGROUND

This disclosure relates to processes designed to treat mono ethylene glycol ("MEG") used in the oil and gas industry to control hydrates formation. More particularly, the disclosure relates to MEG reclamation processes which are designed to remove salts from a wet MEG feed stream.

In the oil and gas industry, dry (lean) MEG is used to control the formation of hydrates within a produced stream. Once used, the now wet (rich) MEG is, in turn, dried and cleaned by way of a MEG regeneration and reclamation process so the MEG can be used again in hydrate control. The systems and methods used to recover MEG usually include three sections: pre-treatment, flash separation, and MEG regeneration. These sections can be followed by salt management and followed or preceded by a calcium removal section.

The MEG used for hydrate inhibition in natural gas pipelines has a similar volatility to organic acids such as acetic acid. Therefore, if water from a well contains organic acids, the organic acid tends to stay with the MEG solution. Removing this organic acid can require large, costly and wasteful blowdown or purges of MEG.

Other options for the removal of organic acid from rich MEG include boiling off the organic acids, distillation of the rich MEG and organic acid, and precipitation using divalent cations. The boiling off method requires a relatively large heating duty to heat the whole stream and/or vacuum conditions. Because the relative volatilities of MEG and organic acid are similar this method also produces large MEG losses. The distillation method, similar to the boiling off method, requires a large heating (reboiling) and cooling (condensing) duty. Although the MEG losses are reduced by distillation, more equipment is required (e.g., column, reboiler, condenser).

The precipitation method requires the addition of chemicals to increase the pH and a solid separation step such as centrifuge or filtration (see e.g. US 2015/0119609 A1).

SUMMARY

Embodiments of a system and method for removing acetic acid and other short chain fatty acids described as organic acids from a rich mono-ethylene glycol ("MEG") solution include:
  adjusting, if needed, the pH of the rich MEG solution to a pH<4 to ensure the organic acids are in acid form;
  stripping the organic acids from the rich MEG solution by contacting the solution with a gas, the gas being nitrogen or a fuel gas such as methane; and
  stripping organic acids from the gas by contacting the gas with a caustic solution such as a dilute sodium hydroxide solution.

The stripping takes place in respective stripping columns. A portion of the gas exiting the gas/organic acid stripping column can be recycled to the MEG/organic acid stripping column to reduce total gas usage. A portion of the waste stream exiting the gas/organic acid stripping column can be recycled back to the gas/organic acid stripping column to reduce the amount of caustic solution used as well as the amount of waste.

This method can be used as part of a MEG regeneration and reclamation process to remove acetic acid and other short chain fatty acids described as organic acids from rich MEG. The method reduces the amount of blowdown, reduces the overall MEG loss, and does not require boiling off, distillation or precipitation.

Unlike the boiling off method, this method requires no heat input, no vacuum conditions, and has relatively low MEG losses. Unlike the distillation method, this method requires a low energy input, no heat input, much less cooling duty, operates at a much lower and therefore safer temperature, and does not require additional large equipment items like a reboiler or condenser. Unlike the precipitation method, this method operates at a low pH (as normally seen in rich MEG) so pH adjustment is minimized and does not require solid separation which can be expensive, complicated and have a low reliability.

BRIEF DESCRIPTION OF THE DRAWINGS.

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

FIG. 2 is a table showing the results of a simulation of the method of FIG. 1 using PROMAX® software.

ELEMENTS USED IN THE DRAWINGS AND DETAILED DESCRIPTION

Figure 1:
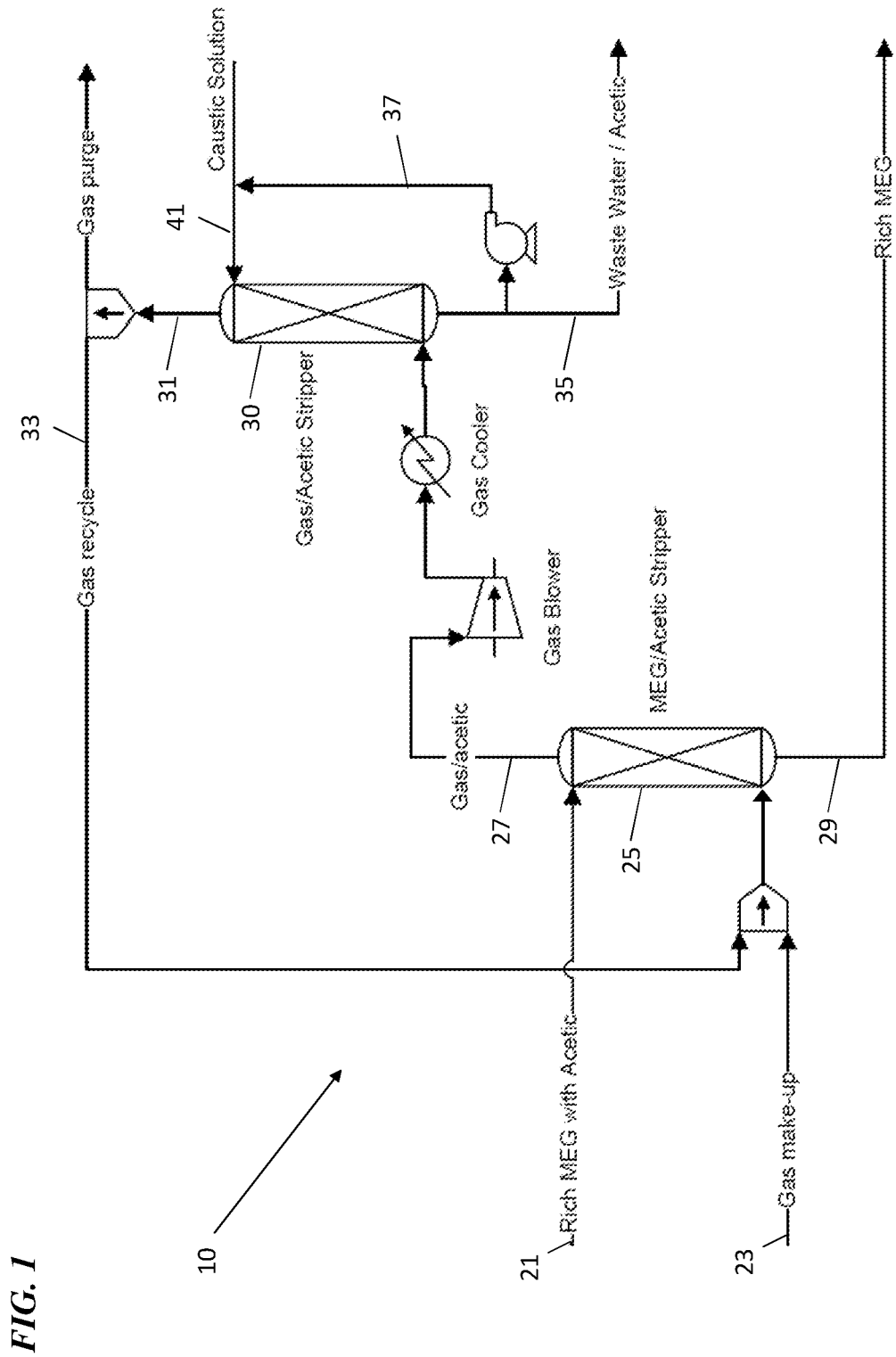
FIG. 1 is an embodiment of the method.

10 System or method
21 Rich MEG solution or stream containing organic acid
23 Gas make-up stream
25 MEG/organic acid stripper column
27 Gas stream containing the organic acid stripped from the 21)
29 Rich MEG stream without or substantially free of the organic acid
30 Gas/organic acid stripper column
31 Gas stream without or substantially free of the organic acid
33 Gas recycle stream portion of 31
35 Waste water stream
41 Solution

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream": "above" and "below"; and other like terms indicating relative positions above or below a given point or element are used in this description to more clearly describe some embodiments of the disclosure.

For the purpose of this disclosure, an "organic acid" is a carboxylic acid having a general formula R—C(O)OH, where R is H (formic acid), $CH_3$ (acetic acid), $CH_3CH_2$ (propionic acid), or $CH_3(CH_2)_2$ (butyric acid)) and where the total number of carbon atoms C is no greater than 4.

Referring to FIG. 1, a wet or rich MEG stream 21 containing an organic acid is routed to a MEG/organic acid stripper column 25 where the rich MEG stream 21 is contacted by a gas make-up stream 23 or gas recycle stream 33 (or some combination of the streams 23, 33). Gas 23, 33 can be a fuel gas such as natural gas or can be nitrogen. The pH of the rich MEG stream 21 can be monitored and adjusted when needed to a pH<4. This helps ensure the organic acid is in acid form.

The gas 23, 33 that has stripped the organic acid from the stream 21 exits a top end of the MEG/organic acid stripper column 25 as a gas stream 27 containing the organic acid. A rich MEG stream 29 without organic acid (or substantially free of organic acid) exits a bottom end of the column 25. "Substantially free of organic acid" means at least 90% of the acetic acid present in the rich MEG stream 21 is removed. If other organic acids are present in stream 21, in embodiments at least 50% of those organic acids are also stripped from the rich MEG stream 21.

The gas stream 27 containing the organic acids stripped from stream 21 is routed to a gas/organic acid stripper column 30 where the stream 27 is contacted by the solution 41. Solution 41 can be a dilute sodium hydroxide solution (e.g., 1.0 wt % NaOH and water) or its equivalent. A gas stream 31 without organic acid (or substantially free of organic acid) exits at the top end of the column 30. "Substantially free of organic acid" means at least 90% of the acetic acid is stripped from the gas stream 27 containing organic acids. In embodiments at least 95% is removed.

A waste water stream 35 containing organic acid exits the bottom end of the gas stripper column 25. This stream 35 can be recycled to the gas/organic acid stripper column 30. The gas stream 31 can be recycled to the MEG/organic acid stripper column 25 as a recycle gas stream 33.

In embodiments, the temperature range operated in is about 40° C. to 60° C., with 60° C. for the rich MEG stream 21 and gas stream 27 containing organic acids, 40° C. for the gas make-up and recycle streams 23, 33, and 40° for solution 41 and water streams. Those temperatures can vary depending on the application-specific requirements.

Referring to FIG. 2, and by way of example only, a simulation using a rich MEG stream of 50.85 m³/hr containing 1497 ppm acetic acid shows that 94% of the acetic acid can be stripped from the rich MEG stream by circulating 1100 kg/hr of stripping gas in the MEG/organic acid stripping column, where 100 kg/hr is provided by the gas make-up flow and 1000 kg/hr is provided by the recycled gas flow. The method also removes 57% of the incoming propionic acid, 99% of the formic acid, and 72% of the butyric acid.

The use of a caustic solution such as a dilute sodium hydroxide solution in the gas/organic acid stripper removes >99% of the acetic acid from the stripping gas. About 90% of the now substantially organic acid-free stripping gas is then recycled in the MEG/organic acid stripper column. This minimizes the amount of stripping gas make-up. A portion of the caustic solution can also be recycled to minimize the amount of caustic and water make-up as well as reduce the waste stream exiting the gas/organic acid stripper column.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:

1. A method for removing organic acid from a rich MEG stream, the organic acid being a carboxylic acid having no more than 4 carbon atoms, the method comprising the step of stripping the organic acid from the rich MEG stream by contacting the rich MEG stream with a gas in a MEG/organic acid stripping column, wherein the rich MEG stream exits the MEG/organic acid stripping column substantially free of the organic acid and the gas exits the MEG/organic acid column containing organic acid stripped from the rich MEG stream.

2. A method according to claim 1 further comprising the step of stripping the organic acid contained in the gas that exits the MEG/organic acid column by contacting the gas with a caustic solution when in a gas/organic acid stripping column, wherein the gas exits the gas/organic acid stripping column substantially free of the organic acid and a waste stream exits the gas/organic acid stripping column containing organic acid stripped from the gas and a portion of the caustic solution.

3. A method according to claim 2 further comprising the step of recycling a portion of the gas exiting the gas/organic acid stripping column for use in the MEG/organic acid stripping column.

4. A method according to claim 2 further comprising the step of recycling a portion of the waste stream back to the gas/organic acid column.

5. A method according to claim 2 wherein the caustic solution is a sodium hydroxide solution comprising about 1% sodium hydroxide.

6. A method according to claim 1 further comprising the step of adjusting, when needed, the pH of the rich MEG stream to a pH<4.

7. A method for removing organic acid from a rich MEG stream, the organic acid being a carboxylic acid, the method comprising the steps of:
    stripping the organic acid from the rich MEG stream by contacting the rich MEG stream with a gas in a MEG/organic acid stripping column, wherein the rich MEG stream exits the MEG/organic acid stripping column substantially free of the organic acid and the gas exits the MEG/organic acid column containing organic acid stripped from the rich MEG stream;
    stripping the organic acid contained in the gas that exits the MEG/organic acid column by contacting the gas with a caustic solution when in a gas/organic acid stripping column, wherein the gas exits the gas/organic acid stripping column substantially free of the organic acid and a waste stream exits the gas/organic acid stripping column containing organic acid stripped from the gas and a portion of the caustic solution.

8. A method according to claim 7 wherein the carboxylic acid has no more than 4 carbon atoms.

9. A method according to claim 7 further comprising the step of recycling a portion of the gas exiting the gas/organic acid stripping column for use in the MEG/organic acid stripping column.

10. A method according to claim 7 further comprising the step of recycling a portion of the waste stream back to the gas/organic acid column.

11. A method according to claim 7 wherein the caustic solution is a sodium hydroxide solution comprising about 1% sodium hydroxide.

12. A method according to claim 7 further comprising the step of adjusting, when needed, the pH of the rich MEG stream to a pH<4.

* * * * *